US00PP28530P2

(12) United States Plant Patent
Lannes

(10) Patent No.: US PP28,530 P2
(45) Date of Patent: Oct. 17, 2017

(54) ***HIBISCUS* PLANT NAMED 'LANWABASH'**

(50) Latin Name: *Hibiscus rosa-sinensis*
Varietal Denomination: Lanwabash

(71) Applicant: Robert M. Lannes, Malause (FR)

(72) Inventor: Robert M. Lannes, Malause (FR)

(73) Assignee: D.H.M. INNOVATION, Malause (FR)

( * ) Notice: Subject to any disclaimer, the term of this patent is extended or adjusted under 35 U.S.C. 154(b) by 0 days.

(21) Appl. No.: 15/330,114

(22) Filed: Aug. 9, 2016

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hibiscus* named 'Lanwabash' that is characterized by its flower colors that are vivid orange with bright pink centers, its floriferous bloom habit with flowers that stay open for 2 to 3 days, its uniform, early blooming and freely flowering habit, its compact and self-branching growth habit and its foliage that is resistant to pathogens common to *Hibiscus*, including *Pseudomonas* sp., *Phythium* sp., and *Phytophthora* sp.

2 Drawing Sheets

Botanical classification: *Hibiscus rosa-sinensis.*
Cultivar designation: 'Lanwabash'.

BACKGROUND OF THE INVENTION

The present invention relates to a new and distinct cultivar of *Hibiscus rosa-sinensis* named 'Lanwabash' and will be referred to hereafter by its cultivar name, 'Lanwabash'. 'Lanwabash' is a new cultivar of tropical *hibiscus* grown for use as a landscape and container plant.

The new cultivar was developed through an ongoing breeding program conducted by the Inventor in Malause, France. The objectives of the breeding program are to develop new cultivars of *Hibiscus* that exhibit large and brightly colored flowers, self-branching, high flower bud counts, and compact plant habits.

'Lanwabash' arose from a controlled cross made by the Inventor in July of 2009 between unnamed proprietary plants of *Hibiscus rosa-sinensis* from the breeding program; reference no. si 238-1 (not patented) as the female parent and reference no. si 443-1 (not patented) as the male parent. 'Lanwabash' was selected as a single unique plant from the resulting seedlings in September of 2013.

Asexual propagation of the new cultivar was first accomplished by stem cuttings in Malause, France in June of 2012 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics the new cultivar. These attributes in combination distinguish 'Lanwabash' as a new and distinct cultivar of *Hibiscus.*

1. 'Lanwabash' exhibits flowers that are vivid orange in color with bright pink centers.

2. 'Lanwabash' exhibits a floriferous bloom habit with flowers that stay open for 2 to 3 days.
3. 'Lanwabash' exhibits a uniform, early blooming and freely flowering habit.
4. 'Lanwabash' exhibits a compact and self branching growth habit.
5. 'Lanwabash' exhibits foliage that is resistant to pathogens common to *Hibiscus*, including *Pseudomonas* sp., *Phythium* sp., and *Phytophthora* sp.

The female parent of 'Lanwabash' differs from 'Lanwabash' in having much smaller flowers that are apricot in color with a lower bud count. The male parent of 'Lanwabash' differs from 'Lanwabash' in having flowers that are red in color and in having a less branched and less compact plant habit. 'Lanwabash' can be most closely compared to the *Hibiscus* cultivars 'Cherie' (not patented) and 'Maple Sugar' (U.S. Plant Pat. No. 16,286). 'Cherie' is similar to 'Lanwabash' in having glossy evergreen leaves that are tolerant to heat and sun and in being floriferous blooming all season. 'Cherie' differs from 'Lanwabash' in having a less compact with a less self-branching plant habit and in having flowers that are a less vivid orange with a red center. 'Maple Sugar' is similar to 'Lanwabash' in having a floriferous blooming habit all season. 'Maple Sugar' differs from 'Lanwabash' in having leaves that are deeply crenate, a less compact plant habit, and flowers that are burgundy in color.

BRIEF DESCRIPTION OF THE DRAWINGS

The accompanying colored photographs illustrate the overall appearance and distinct characteristics of the new *Hibiscus*. The photographs were taken of an 18 month-old plant of 'Lanwabash' as grown in a two-gallon container.

The photograph in FIG. 1 provides a side view of 'Lanwabash' in bloom.

Figure 1:
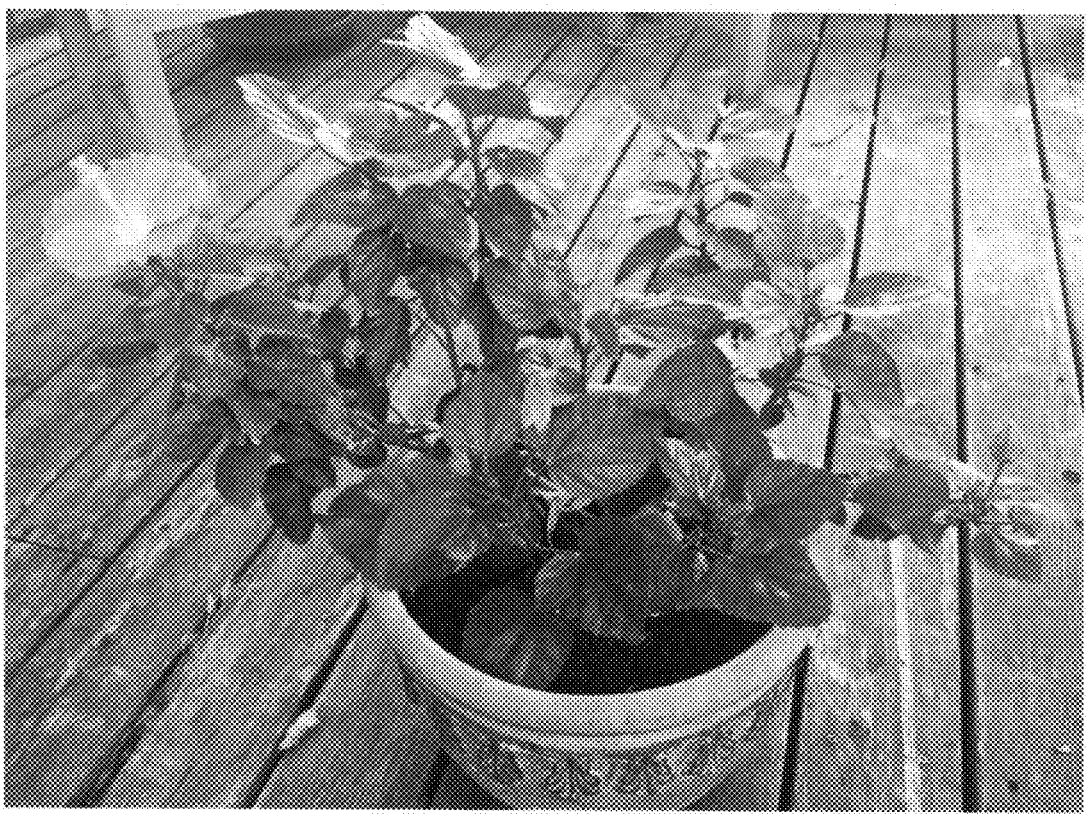
Figure 2:
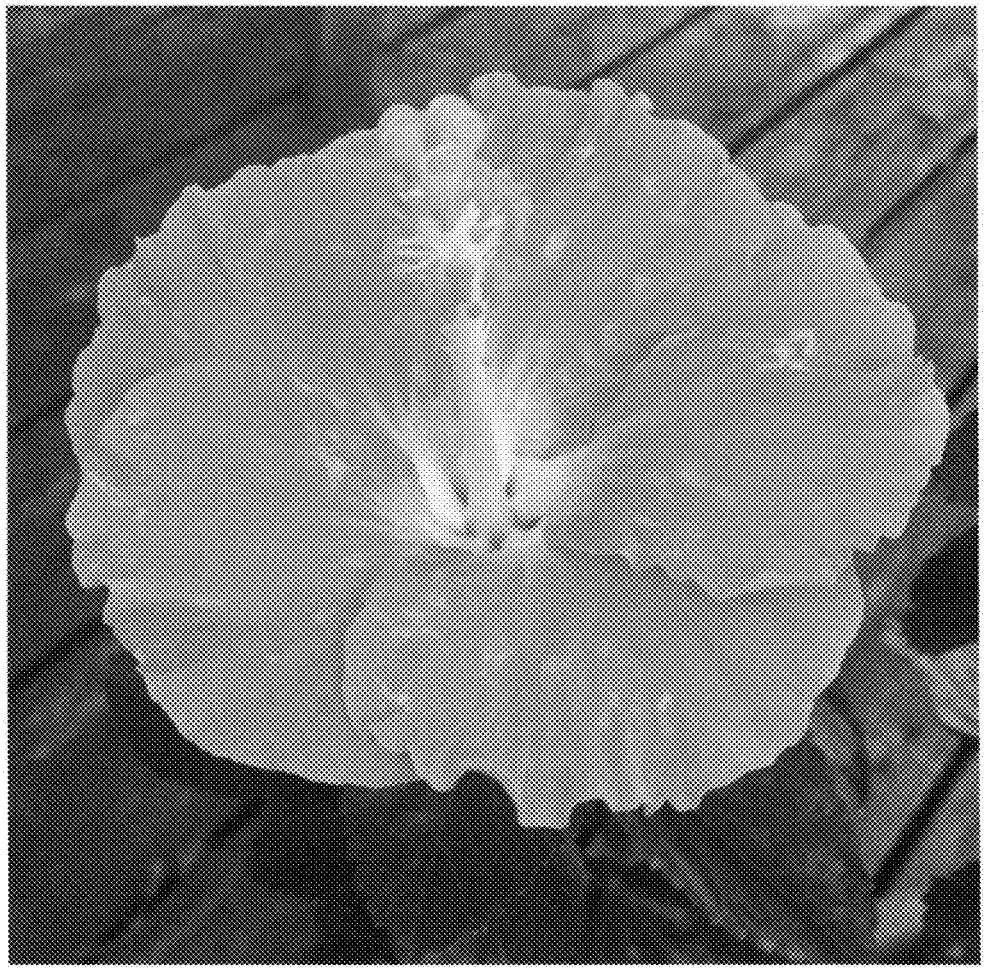

The photograph in FIG. 2 provides a close-up view of a flower of 'Lanwabash'.

The colors in the photographs are as close as possible with the photographic and printing technology utilized and the color values cited in the Detailed Botanical Description accurately describe the colors of the new *Hibiscus*.

DETAILED BOTANICAL DESCRIPTION OF THE PLANT

The following is a detailed description of 18 month-old plants of the new cultivar as grown in two-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period*.—Continuously producing in warm temperatures 55° F. to 90° F.

*Plant type*.—Tropical evergreen shrub.

*Plant habit*.—Compact and self-branching.

*Height and spread*.—An average of 40 cm in height and 38 cm in spread as grown in a two-gallon container and reaches an average of 0.9 m in height and 1.5 cm in spread when mature in the landscape.

*Hardiness*.—Tropical; at least in U.S.D.A. Zones 9 to 10.

*Diseases*.—Resistance to pathogens common to *hibiscus*, including *Pseudomonas*. sp, *Phythium* sp., and *Phytophthora* sp.

*Root description*.—Fibrous roots, 161A in color.

*Propagation*.—Stem cuttings.

*Root development*.—Roots initiate in about 56 days and develop as a young plant in about 6 months.

*Growth rate*.—Moderately vigorous.

Stem description:

*Shape*.—Round.

*Stem color*.—New growth; 138B, mature wood; 197B and 197A.

*Stem size*.—Main branch; an average of 25 cm in length and 1 cm in width, lateral branch; an average of 21 cm in length and 6 mm in width.

*Stem surface*.—New growth; glabrous, mature wood; bark-like, finely striated.

*Stem aspect*.—Held at various angles ranging between 60° and 80° (90°=straight upright, vertical).

*Stem strength*.—Very strong.

*Branching*.—Heavily pinched; main stems; an average of 4, lateral branches an average of 2 per main branch.

*Internode*.—Average of 2.5 cm.

*Stipules*.—1 per leaf node, ovate in shape, an average of 1.5 cm in length and 1 cm in width, both surfaces rough and pubescent surface, bluntly acute apex, acute base, slightly serrate margins, both surfaces 143A in color.

Foliage description:

*Leaf shape*.—Ovate.

*Leaf division*.—Simple.

*Leaf base*.—Cuneate.

*Leaf apex*.—Acute.

*Leaf venation*.—Pinnate, vein color matches surface of the leaf.

*Leaf margins*.—Serrate and wavy, tips of serration have a small mucronate tip.

*Leaf attachment*.—Petiolate.

*Leaf arrangement*.—Alternate.

*Leaf orientation*.—Horizontal to petiole.

*Leaf aspect*.—Primarily flat with wavy margins.

*Leaf surface*.—Upper surface slightly glossy and dull, leathery texture, lower surface very finely puberulent and dull, leathery texture.

*Leaf color*.—Young and mature leaves upper surface 137A, lower surface 138A.

*Leaf size*.—An average of 9 cm in length, and 8 cm in width when mature.

*Leaf quantity*.—An average of 26 leaves per a stem 40 cm in length.

*Petioles*.—An average of 3 cm in length and 2 mm in diameter, 144A in color, finely pubescent and slightly glossy surface.

Flower description:

*Inflorescence type*.—Flowers are solitary from upper leaf axils.

*Lastingness of flowers*.—An average of 2 to 3 days, self cleaning.

*Flower size*.—An average of 9 cm in depth (including calyx) and 11.5 cm in diameter.

*Flower fragrance*.—None.

*Flower shape*.—Rotate.

*Flower number*.—Average of 1 to 2 open flowers and 3 buds per lateral stem.

*Flower aspect*.—Outward to upright.

*Flower bud*.—Elliptic in shape, an average of 5 cm in length and 2 cm in width, a blend of 26A, 28A, 33A and 11A in color, glabrous surface.

*Petals*.—5, 40% fused, overlapping, oblanceolate in shape, an average of 6 cm in length and 6 cm in width, slightly serrate and wavy margins, rounded apex, base is cuneate slightly oblique and adnate to base of style re-curved, lower surface is glossy, upper surface is satiny and waxy near the base (throat), color of upper surface N25B, base (throat) is a blend of 11D and 68C, color lower surface a blend of 30B, 26B and 14C, base (throat) is a blend of 11D and a slight flush of 68C.

*Calyx*.—Campanulate in shape, average of 3 cm in length and 2 cm in diameter.

*Epicalyx*.—Comprised of 9 bracts held upright surrounding sepals, lanceolate in shape, apiculate apex, truncate base, average of 1.5 cm in length and 2 mm in width, color of both surfaces is 143A and flushed with 144A at the base, both surfaces are dull.

*Sepals*.—5, base 60% fused, an average of 1 cm in length and 7 mm in width, color of both surfaces is a blend of 143A and 144A, outer surface is rough and slightly puberulent, inner surface is glossy and smooth, acute apex, truncate base.

*Peduncles*.—An average of 4 cm in length and 3 mm in diameter, strong, average angle upright to outward, 144A in color, surface is rough and slightly glossy.

*Pedicels*.—Not present, flowers are solitary from terminal leaf axils.

*Receptacle*.—1 cm in diameter, a blend of 150C in color, glabrous and glossy surface.

Reproductive organs:

*Gynoecium.*—1 pistil, stigmas; 5, round in shape, 2 mm in diameter, surface covered with short fuzzy hairs, 17A in color, style arms; 5 mm in length, 1 mm in diameter, 12D in color, surface is moderately covered with long hairs 1 mm in length matching the surface color, style; average of 3.5 cm in length, glossy surface, 11C in color, ovary; orbicular in shape with round apex, surface is covered with short fuzzy hairs, 7 mm in length and width, 150C in color.

*Androecium.*—Stamens; average of 50, stamens are clustered and implanted into upper portion of style, anthers; dorsifixed in shape, 1 mm in diameter, and 17A in color; filament; 5 mm in length and NN155C in color, pollen; moderate in quantity and 17A in color.

*Fruit/seeds.*—None observed to date.

It is claimed:

1. A new and distinct cultivar of *Hibiscus* plant named 'Lanwabash' as herein illustrated and described.

* * * * *